United States Patent [19]

Webb

[11] 4,362,878
[45] Dec. 7, 1982

[54] SUBSTITUTED 1,2,4-TRIAZOLES AS DIR COMPOUNDS AND THEIR USE IN PHOTOGRAPHIC MATERIALS

[75] Inventor: Terence C. Webb, Witham, England

[73] Assignee: Ciba-Geigy AG, Basel, Switzerland

[21] Appl. No.: 158,979

[22] Filed: Jun. 12, 1980

Related U.S. Application Data

[62] Division of Ser. No. 72,735, Sep. 5, 1979, Pat. No. 4,259,437.

[30] Foreign Application Priority Data

Sep. 18, 1978 [GB] United Kingdom ............... 37260/78

[51] Int. Cl.³ .................. C07D 249/12; C07D 403/06
[52] U.S. Cl. .................................... 548/253; 548/264; 548/265
[58] Field of Search ........................ 548/253, 264, 265

[56] References Cited

U.S. PATENT DOCUMENTS

| | | | |
|---|---|---|---|
| 3,869,291 | 3/1975 | Madey et al. | 430/544 |
| 3,945,829 | 3/1976 | Zorn et al. | 548/265 |
| 4,079,143 | 3/1978 | Balasubramanyan et al. | 542/400 |
| 4,121,934 | 10/1978 | Yagihara et al. | 430/544 |

Primary Examiner—Alton D. Rollins
Attorney, Agent, or Firm—Joseph G. Kolodny

[57] ABSTRACT

Development inhibitor releasing compounds of the formula:

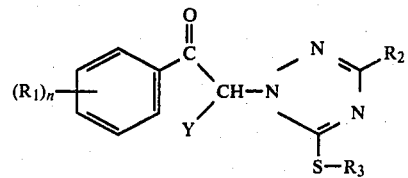

are provided wherein $R_1$ is hydrogen or a substituent which may contain a long chain ballasting group and n is 1 or 2, or $R_1$ may form an annelated ring, $R_2$ is hydrogen or alkyl having 1 to 4 carbon atoms, $R_3$ is alkyl, aryl or aralkyl, Y is hydrogen, halogen, optionally substituted phenyl, —COOR$_4$, —COR$_4$,

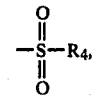

or —OR$_4$ where $R_4$ is alkyl or aryl or a group

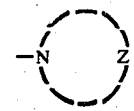

where Z represents the atoms necessary to complete an optionally substituted 5- or 6-membered heterocyclic ring which optionally may be benzannelated.

The new DIR-compounds form colorless compounds when reacted with the oxidation products of the color developing agent. They have an extremely high reactivity with the oxidation products of the color developing agent so that only small quantities of the DIR-compounds are required to produce excellent intra-image and inter-image effects of excellent speed.

7 Claims, No Drawings

SUBSTITUTED 1,2,4-TRIAZOLES AS DIR COMPOUNDS AND THEIR USE IN PHOTOGRAPHIC MATERIALS

This is a division of application Ser. No. 072,735, filed Sept. 5, 1979, now U.S. Pat. No. 4,259,437, issued Mar. 31, 1981.

The present invention relates to novel chemical compounds and to their use as photographic development inhibitor releasing compounds. Development inhibitor releasing compounds are hereinafter referred to as D.I.R. compounds.

According to the present invention there are provided compounds of the general formula:

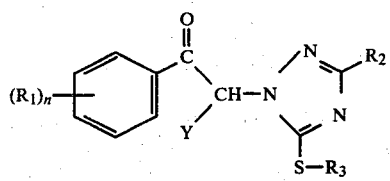 (1)

wherein $R_1$ is hydrogen or a substituent which may contain a long chain ballasting group and n is 1 or 2, or $R_1$ may represent the atoms necessary to complete an annelated ring, $R_2$ is hydrogen or alkyl having 1 to 4 carbon atoms, $R_3$ is alkyl, aryl or aralkyl, Y is hydrogen, halogen, optionally substituted phenyl, —COOR$_4$, —COR$_4$,

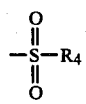

or —OR$_4$ where R$_4$ is alkyl, aryl or a group

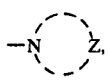

where Z represents the atoms necessary to complete an optionally substituted 5- or 6-membered heterocyclic ring which optionally may be benzannelated.

Preferably there is present in the compound a long chain alkyl ballasting group. This group may be present in $R_1$ or it may be present in Y when Y is the group

or it may be $R_3$.

Examples of $R_1$ are hydrogen, hydroxy, halogen, (fluorine, chlorine, bromine), nitro, hydroxymethyl, alkyl or alkoxy of 1 to 18 carbon atoms, —NHCOR$_4$, —NHSO$_2$R$_4$, —COOR$_4$, —NH$_2$, —COOH, —SH, —SR$_4$ where R$_4$ is as defined above.

Preferred meanings of $R_1$ are hydrogen, hydroxy, halogen (bromine) or alkoxy of 6 to 18 carbon atoms.

Preferably Y is hydrogen, halogen (chlorine, bromine), optionally substituted phenyl or a group

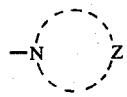

as defined above.

Preferably the group

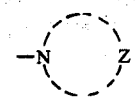

is an optionally substituted triazole, tetrazole, benzimidazole, urazole, pyrazole, phthalimido or succinimido group; triazoles, benzimidazoles and urazoles are mostly preferred.

Suitable substituents are alkyl of 1 to 4 carbon atoms, alkylmercapto of 1 to 8 carbon atoms, nitro, phenyl and/or benzyl.

A preferred class of the compounds of formula (1) are those of formula:

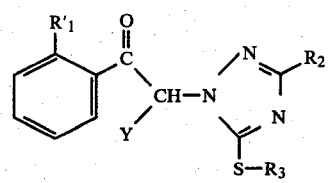 (2)

wherein Y, R$_2$ and R$_3$ are as defined above and R$_1$' is hydroxy, alkoxy of 1 to 18, preferably of 6 to 18 and most preferably of 12 to 18 carbon atoms or halogen (bromine).

Conveniently the alkoxy group has an alkyl moiety containing at least 6 carbon atoms which helps to render the compound substantive in any layer in which it is coated and also helps to render it oil soluble.

Also preferably in the compounds of formula (2) R$_2$ is hydrogen and R$_3$ is alkyl having from 4 to 12 carbon atoms.

A particularly preferred class of compounds of formula (2) are compounds of the general formula:

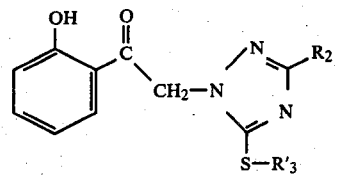 (3)

wherein R$_3$' is alkyl having from 6 to 12 carbon atoms.

Another preferred class of compounds of formula (2) are the compounds of formula:

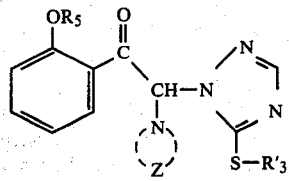 (4)

where R$_5$ is alkyl having at least 12 carbon atoms, R$_3$' is alkyl having from 6 to 12 carbon atoms and the group

is an optionally substituted triazole, tetrazole, benzimidazole, urazole, pyrazole, phthalimido or succinimido group, with substituents as mentioned above.

Another useful class of compounds of formula (1) are compounds of formula:

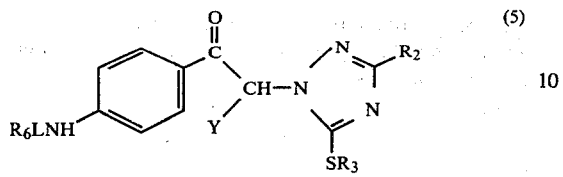

where Y, $R_2$ and $R_3$ are as defined above and L is a $-SO_2$ or $-CO-$ link and $R_6$ is alkyl comprising at least 12 carbon atoms or is a group which comprises such an alkyl group.

The compounds of formula (1) couple with the oxidation products of a colour developing compound of the paraphenylene diamine type to yield a colourless coupler and the alkylthiotriazole group is liberated. This group is a D.I. compound.

According to another aspect of the present invention there is provided a light-sensitive photographic material which comprises, coated on a photobase, at least one silver halide emulsion layer, the said emulsion layer or a layer adjacent thereto comprising a compound of the general formula (1).

Preferably the compound of formula (1) is present in the silver halide emulsion layer.

In the preferred compounds of Formula (4) both the group:

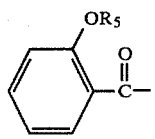

and the group

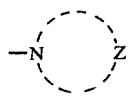

which are attached to the central methine group of the compound are electron withdrawing groups. This means that the methine group is an activated methine group which can couple with oxidised colour developers of the paraphenylene diamine type in the same way as colour couplers couple with such oxidised colour developers. The coupling of the compound of formula (1) with oxidised colour developer leads to an unstable compound in which elimination occurs and the alkylthiotriazole group is released.

Release of the alkylthiotriazole group from the compound of formula (1) also occurs on the coupling reaction with oxidised colour developer when Y in formula (1) is hydrogen, but not so readily in the compounds of formula (3).

When Y is halogen release of the alkylthiotriazole occurs readily but some loss of photographic speed of the photosensitive silver halide emulsion is found to occur. The alkylthiotriazole is more efficacious as a D.I. compound when $R_2$ is hydrogen and $R_3$ is alkyl having from 4 to 12 carbon atoms.

Thus preferably in the compound of formula (1) $R_2$ is hydrogen and $R_3$ is alkyl having from 4 to 12 carbon atoms.

The alkylthiotriazoles are released readily during the coupling reaction with oxidised colour developer when Y is the group

without any concomitant loss of speed of the emulsion.

Thus preferably in the compound of formula (1), Y is the group

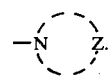

Also preferably the ballasting group is part of $R_1$.

By ballasting alkyl group is meant a straight or branched chain alkyl group, optionally substituted, having at least 6 carbon atoms. The presence of the ballasting alkyl group in the D.I.R. compound renders this compound substantive to the layer in which it is coated.

Compounds of the above formula (1) may be prepared by reacting a solution of a compound of the general formula:

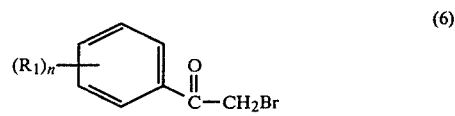

with an alkylthiotriazole of the general formula:

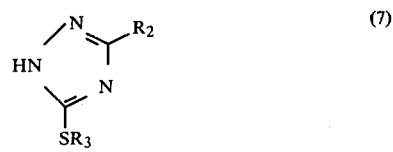

wherein $R_1$, $R_2$ and $R_3$ have the meanings assigned to them above, to yield a compound of formula:

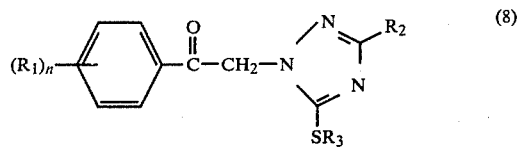

This is a compound of formula (1) when Y is hydrogen.

Compounds of formula (8) may be converted to compounds of formula (1) where Y is halogen by halogenation of the compound of formula (8) either in chloroform or in acetic acid medium. For example bromination in chloroform medium yields a compound of the general formula:

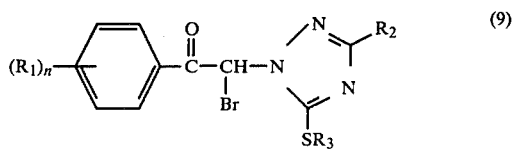

Compounds of formula (9) may be converted to compounds of formula (1) for example wherein Y is the group

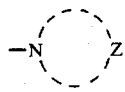

by reacting compounds of formula (9) with a compound of the formula:

in the presence of a base or with a potassium salt

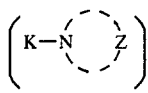

in acetonitrile.

Preferably the base used in the above preparations is pulverised potassium hydroxide.

The alkylthiotriazole compound which is of formula (7) is a D.I. compound. The use of compounds which release D.I. compounds imagewise is well known in the photographic art to produce useful inter-layer and intra-layer effects.

While various development inhibitor-releasing compounds have been produced hitherto the majority of these compounds are not completely satisfactory. For example in the case of a development inhibitor releasing compound which forms a dye upon colour development, the colour coupler residue of the D.I.R. compound must be carefully selected to achieve the correct colour balance in the photographic colour image because of the specific absorption properties required of the resulting dye. It has proved difficult to produce useful D.I.R. colour couplers.

On the other hand those development inhibitor releasing compounds which form no dye with the oxidation products of a colour developing agent either possess extremely low reactivity or cause serious speed loss during development.

However the compounds of the present invention form colourless compounds when reacted with the oxidation products of the colour developing agent. The colourless residue does not constitute any part of the resulting image. This has the advantage that the novel releasing compounds can be applied to any required layer in the photographic material. Furthermore, the compounds of the present invention have an extremely high reactivity with the oxidation products of the colour developing agent. Consequently only small quantities of compound are required to produce excellent intra-image and inter-image effects without serious speed losses.

In yet another aspect of the present invention there is provided a process for the production of a photographic image which comprises imagewise exposing a light-sensitive photographic silver halide material which comprises in at least one silver halide layer or a layer adjacent thereto a compound of formula (1) and developing the exposed silver halide with a paraphenylenediamine colour developing agent thereby to liberate imagewise the alkylthiotriazole compound of formula (7).

The D.I.R. compounds of the present invention may be used in any photographic product which can be processed by a chromogenic process and in which increased image sharpness and/or interlayer effects are desired. Thus the greatest use of the D.I.R. compounds of the present invention is expected to be in the field of colour photographic material and in particular in colour negative film material. When used in colour film material it is expected that the D.I.R. compounds of the present invention will be present in colour-sensitised silver halide emulsion layers which comprise at least one colour coupler. Useful amounts of D.I.R. present in such silver halide emulsion layers are 5-10 mole % of the colour coupler present.

Examples of specific compounds according to the present invention which release a development inhibitor compound on coupling are:

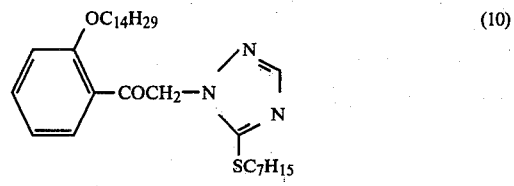

(10)

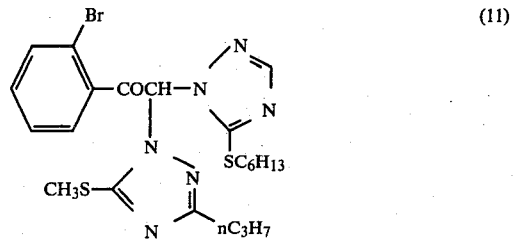

(11)

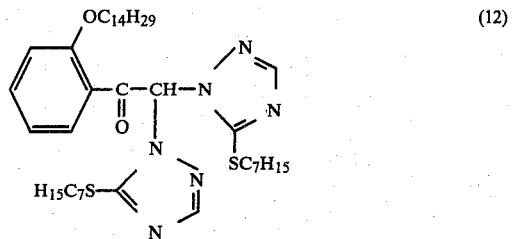

(12)

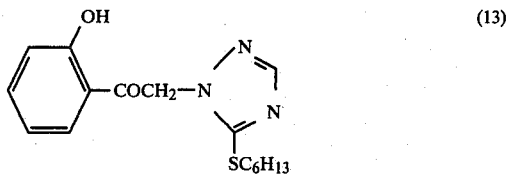

(13)

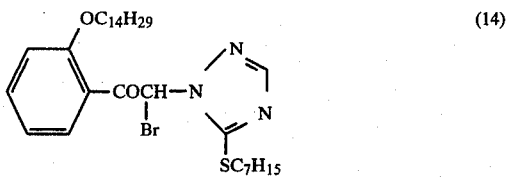

(14)

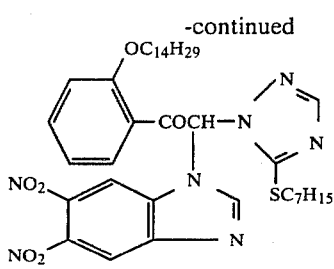
(15)

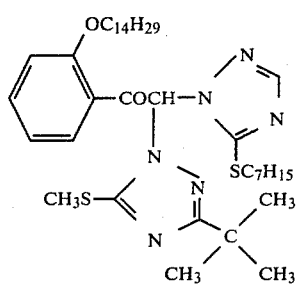
(16)

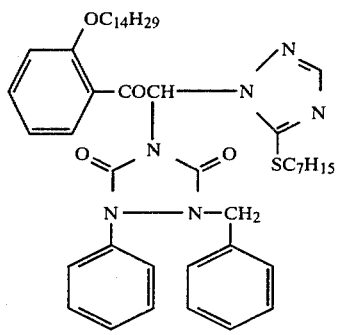
(17)

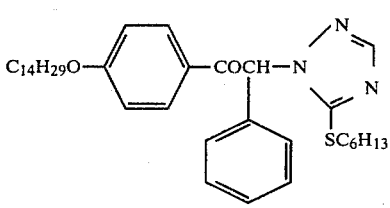
(18)

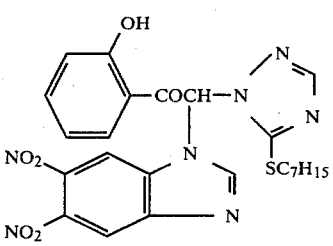
(19)

In the following Examples parts and percentages are by weight.

EXAMPLE 1

Preparation of 2-[3(5)-heptylthiotriazolyl]-2'-tetradecyloxyacetophenone (compound of formula (10))

A solution of 2'-tetradecyloxyphenacyl bromide (10 g) in warm acetonitrile (30 ml) was added to a solution of 3(5)-heptylthiotriazole (6 g) and triethylamine (3 g) in acetonitrile (20 ml). The reaction mixture was stirred at room temperature for 6 hours and then evaporated. The residue was dissolved in ethyl acetate (50 ml) and the organic layer washed with water (2×50 ml), dried over MgSO$_4$, filtered and evaporated. Recrystallisation of the residue from methanol gave the compound of formula (10) as a fine white powder (7.8 g, 61%) m.p. 61°-62° C. (Found: C, 69.97; H, 9.41; N, 7.91% C$_{31}$H$_{51}$N$_3$O$_2$S requires: C, 70.27; H, 9.70; N, 7.93%).

EXAMPLE 2

Preparation of 2-bromo-[3(5)-heptylthiotriazolyl]-2'-tetradecyloxyacetophenone (compond of formula (14))

To a stirred solution of compound 10 (5.1 g) in chloroform (75 ml) at 60° C. was added over a period of 2 hours a solution of bromine (1.6 g) in chloroform (10 ml). The reaction mixture was stirred at reflux temperature for a further 2 hours and then evaporated. Trituration of the residual oil in methanol at 0° C. afforded the product in solid form. Subsequent filtration gave the compound of formula (14) as a fine white powder (5.4 g, 92%) m.p. 45°-46° C. (Found: C, 60.85; H, 8.20; N, 7.1%. C$_{31}$H$_{50}$BrN$_3$O$_2$S requires: C, 61.11; H, 8.27; N, 6.9%).

EXAMPLE 3

Preparation of 2-[3(5)-heptylthiotriazolyl]-2-[5,6-dinitrobenzimidazolyl]-2'-tetradecyloxyacetophenone (compound of formula (15))

A mixture of the potassium salt of 5,6-dinitrobenzimidazole (2.6 g) and 2-bromo-2-[3(5)-heptylthiotriazolyl]-2'-tetradecyloxyacetophenone (5.3 g) in acetonitrile (50 ml) was stirred at 40° C. for 5 hours then evaporated. The residue was dissolved in chloroform and the organic layer washed with water (2×50 ml), dried over MgSO$_4$, filtered and evaporated. Recrystallisation of the residue from methanol gave the compound of the formula (15) as a white solid (4.44 g, 68%) m.p. 63°-64°. (Found: C, 61.80; H, 7.30; N, 12.72%. C$_{38}$H$_{53}$N$_7$O$_6$S requires C, 62.01; H, 7.25; N, 13.04%).

EXAMPLE 4

Preparation of 2-[3(5)-heptylthiotriazolyl]-2-[3-t-butyl-5-methylthiotriazolyl]-2'-tetradecyloxyacetophenone (compound of formula (16))

A solution of the potassium salt of 3-t-butyl-5-methylthio triazole (2.1 g) in acetonitrile (25 ml) was added to 2-bromo-2-[3(5)-heptylthiotriazolyl]-2'-tetradecyloxyacetophenone (6.0 g) in acetonitrile (50 ml). The reaction mixture was stirred at 45° C. for 31/2 hours then evaporated. The residue was dissolved n chloroform and the organic layer washed with water, dried over MgSO$_4$, filtered and evaporated. The compound was purified by column chromatography. Recrystallisation from methanol gave the compound of formula (16) as a fine white solid (2.7 g, 39%) m.p. 63° C. (Found: C, 65.36; H, 8.90; N, 11.91% C$_{38}$H$_{62}$N$_6$O$_2$S$_2$ requires: C, 65.28; H, 8.93; N, 12.02%).

EXAMPLE 5

Preparation of 2-[3(5)-heptylthiotriazolyl]-2-N-benzylphenylurazolyl-2'-tetradecyloxyacetophenone (compound of formula (17))

To a solution of 2-bromo-2[3(5)-heptylthiotriazolyl]-2'-tetradecyloxyacetophenone (3.0 g) and benzylphenylurazole (1.4 g) in acetonitrile (35 ml) was added pulverized potassium hydroxide pellets (0.45 g). The reaction mixture was stirred at room temperature for 2 hours, filtered and evaporated. Recrystallisation of the residue from methanol gave the compound of formula (17) as a fine white powder (2.3 g, 58%) m.p. 48°–49° C. (Found: C, 69.17; H, 7.80; N, 10.41%. $C_{46}H_{62}N_6O_4S$ requires: C, 69.40; H, 7.86; N, 10.57%).

EXAMPLE 6

Preparation of 2-[3(5)-hexylthiotriazolyl]-2-phenyl-4'-tetradecyloxyacetophenone (compound of formula (18))

(a) 4-tetradecyloxyphenyl-benzyl ketone

To a solution of 4-hydroxyphenyl-benzyl ketone (10.5 g) in a solution of potassium hydroxide (3.0 g) in ethanol (100 ml) was added tetradecylbromide (16 g). The reaction mixture was stirred at gentle reflux temperature for 12 hours, cooled and poured into water. The product was extracted into chloroform, washed further with water, dried over $MgSO_4$, filtered and evaporated. Recrystallisation of the residue from methanol gave the above compound as a colourless crystalline solid (17.5 g, 86%) m.p. 72°–74° C.

(b) 2-bromo-2-phenyl-4'-tetradecyloxyacetophenone

To the above ketone (8.0 g) in chloroform (50 ml) containing zinc chloride (0.2 g) was added a solution of bromine (3.2 g, 1.1 ml) in chloroform (25 ml). The reaction mixture was stirred at 35° C. for 31/2 hours and evaporated to dryness. Recrystallisation of the residue from methanol afforded the 2-bromo derivative as a fine white solid (8.1 g, 85%) m.p. 62°–65° C.

(c) 2-[3(5)-hexylthiotriazolyl]-2-phenyl-4'-tetradecyloxyacetophenone (compound of formula (18))

To the above 2-bromo compound (4.9 g) and 3(5)-hexylthio-1,2,4-triazole (2.0 g) in acetonitrile (35 ml) was added pulverised potassium hydroxide pellets (0.6 g). The reaction mixture was stirred at room temperature for 6 hours, filtered and evaporated. The residue was triturated at 0° C. in methanol to give the compound of formula (18) as a white solid (2.7 g, 46%) m.p. 54°–58° C. (Found: C, 72.86; H, 9.00; N, 7.10%. $C_{36}H_{53}N_3O_2S$ requires: C, 73.01; H, 9.03; N, 7.13%).

EXAMPLE 7

Preparation of 2-[3(5)-hexylthiotriazolyl]-2'-hydroxyacetophenone (compound of formula (13))

2-[3(5)-Hexylthiotriazolyl]-2'-tetradecyloxyacetophenone (prepared in an analogous manner to the compound of formula (10)) (5.2 g) was stirred at gentle reflux with hydrobromic acid (48%, 60 ml) for 5 hours, cooled and poured into water. The aqueous medium was neutralised with sodium hydroxide solution and extracted with ether. The ether extract was washed with water, dried over $MgSO_4$, filtered and evaporated to give a crystalline product. Trituration of the residue with petrolether (60°–80° C.) gave compound 13 as a white solid (2.3 g, 69%) m.p. 62°–65° C. (Found: C, 60.25; H, 6.64; N, 13.2%. $C_{16}H_{21}N_3O_2S$ requires C, 60.16; H, 6.63; N, 13.16%).

EXAMPLE 8

Preparation of 2-[3(5)-heptylthiotriazolyl]-2-[5,6-dinitro benzimidazolyl]-2'-hydroxyacetophenone (compound of formula (19))

In an analogous manner to the preparation of the compound of formula (13) the compound of formula (19) was prepared from the compound of formula (15) as produced in Example 3 by reaction with hydrobromic acid under reflux conditions for 5 hours.

EXAMPLE 9: (Use example)

1-(2,4,6-Trichlorophenyl)-3-(3-[(2,4-ditertamylphenoxy)acetamido]-benzamido)-5-pyrazolone (10 g) was dissolved in a solution of tricresyl phosphate (10 g) and ethyl acetate (10 g) (coupler emulsion). A solution of gelatin (80 g) was added followed by water (20 ml) and 20 ml of a wetting agent (10% aqueous solution of the sodium salt of diisobutyl naphthalene sulfonic acid). The whole was then dispersed using an ultrasonic mixer.

The above coupler emulsion (24 g) was added to a silver iodobromide emulsion (40 g) having a silver content of 4.9 g and an average iodide content of 8.8 molar percent. Gelatin solution (48 g) and further 3.8 ml of the wetting agent were added and the whole made up to 200 g with water.

The mixture was coated onto subbed triacetate film base to give a silver coating weight of 20 mg per $dm^2$ and a coupler coating weight of 6.4 mg per $dm^2$. Above this was coated a 20 mg per $dm^2$ gelatin layer containing a triazine hardener.

The coating was exposed to a continuous wedge and then subjected to the following processing sequence at 37.8° C.
1. Colour development 3.25 mins
2. Bleaching 6.50 mins
3. Washing 3.25 mins
4. Fixing 6.50 mins
5. Washing 3.25 mins
6. Stablizing 1.50 mins.

The processing baths had the following compositions.

| 1. | Developer | |
|---|---|---|
| | Potassium carbonate | 37.5 g |
| | Sodium metabisulphite (anhydr.) | 4.25 g |
| | Potassium iodide | 2.0 mg |
| | Sodium bromide | 1.3 g |
| | Hydroxylamine sulphate | 2.0 g |
| | 4-(N—ethyl-N—β-hydroxyethylamino)-2-methylaniline sulphate | 4.75 g |
| | Water to 1 liter. | |
| 2. | Bleaching bath | |
| | Ammonium bromide | 150 g |
| | Ferric ammonium ethylenediamine tetra-acetic acid | 175 ml |
| | Glacial acetic acid | 10.5 ml |
| | Sodium nitrate | 35 g |
| | Water to 1 liter. | |
| 4. | Fixing bath | |
| | Ammonium thiosulphate (50%) | 162 ml |
| | Diethylene triamine penta-acetic acid | 1.25 g |
| | Sodium metabisulphite (anhyd.) | 12.4 g |
| | Sodium hydroxide | 2.4 g |
| | Water to 1 liter. | |
| 6. | Stabilizer | |
| | 35% formaldehyde solution | 5.0 ml |
| | Water to 1 liter. | |

The above procedure (CONTROL) produced the following photographic results for maximum contrast (γm) and contrasted adjusted speed (S γ/4):

| Control | γm | S γ/4 (log E units) |
|---|---|---|
| Pyrazolone coupler alone | 1.30 | 2.73 |

To allow for the effect of contrast on foot speed the S γ/4 value has been quoted. This is defined as:

$S\gamma/4 = $ (Speed at a density level of fog) $+ \gamma/4$.

The above coating procedure was then repeated but in addition to the pyrazolone coupler, coatings wer made which individually incorporated 5 or 10 mole percent of D.I.R. compounds, and the percentage γm suppression and change in S γ/4 compared with the control were measured.

TABLE 1

| D.I.R. compound | % γm suppression | Change in S γ/4 |
|---|---|---|
| 5% level of compound (10) | 26 | +0.01 |
| 10% level of compound (10) | 35 | +0.01 |
| 10% level of compound (12) | 19 | +0.03 |
| 5% level of compound (13) | 43 | +0.02 |
| 5% level of compound (14) | 53 | −0.02 |
| 5% level of compound (15) | 38 | +0.01 |

Table 1 clearly shows that the compounds of the present invention can be used to inhibit development as shown by the high γmax suppression values. The compounds can be chosen to provide a range of D.I.R. activity. Furthermore the D.I.R. compounds of the present invention, with the exception of the compound of formula (14), show no speed loss as shown by the positive S γ/4 values.

EXAMPLE 10: (Use example)

Further coatings as prepared in Example 9 were exposed to a line and space chart at a range of exposures and subjected to the processing sequence as before.

Using a microdensitometer the density difference for each line and space frequency were calculated. The relative response was then calculated by normalising the density difference at each frequency to that of the lowest frequency.

As relative response changes with exposure the results quoted were averaged over the exposure range.

TABLE 2

| | Relative Response | |
|---|---|---|
| D.I.R. compound | 7 lines/mm | 35 lines/mm |
| None (pyrazolone coupler alone) | 0.87 | 0.40 |
| 10% level of compound (10) | 0.99 | 0.52 |
| 5% level of compound (13) | 1.01 | 0.56 |
| 10% level of compound (14) | 1.00 | 0.44 |

Table 2 shows clearly that the D.I.R. compounds of the present invention exhibit increased sharpness when compared with the control coating.

I claim:

1. A compound of the general formula:

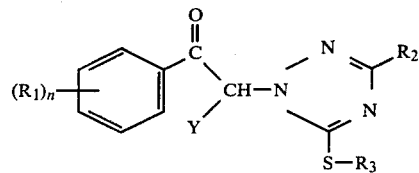

wherein:
$R_1$ is hydrogen, hydroxy, halogen or alkoxy of 6 to 18 carbon atoms, and n is 1 or 2,
$R_2$ is hydrogen or alkyl having 1 to 4 carbon atoms,
$R_3$ is alkyl of 4 to 12 carbon atoms and
Y is hydrogen, halogen, phenyl or a 1, 2, 4-triazole, benzimidazole, tetrazole, urazole, pyrazole, phthalimido or succinimido group, substituted by alkyl of one to four carbon atoms, alkylmercapto of 1 to 8 carbon atoms, nitro, phenyl and/or benzyl.

2. A compound according to claim 1 of the general formula:

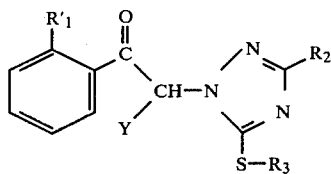

wherein $R_2$, $R_3$ and Y are as defined in claim 1 and $R_1'$ is hydroxy, alkoxy of 6 to 18 carbon atoms or halogen.

3. A compound according to claim 2 wherein $R_1'$ is hydroxy, bromine or alkoxy of 6 to 18 carbon atoms.

4. A compound according to claim 2 wherein $R_2$ is hydrogen.

5. A compound according to claim 2 wherein Y is hydrogen, halogen, phenyl, 1,2,4-triazolyl, benzimidazolyl or urazolyl the nitrogen heterocyclic rings being substituted by alkyl of 1 to 4 carbon atoms, alkylmercapto of 1 to 8 carbon atoms, nitro, phenyl and/or benzyl.

6. A compound according to claim 1 of the general formula:

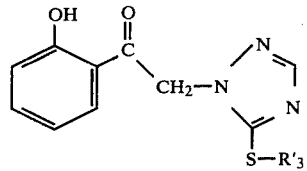

wherein $R_3'$ is alkyl of 6 to 12 carbon atoms.

7. A compound according to claim 1 of the general formula:

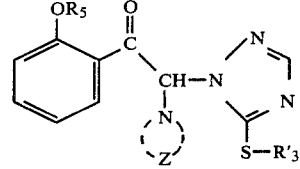

where $R_5$ is an alkyl group of 12 to 18 carbon atoms, $R_3'$ is alkyl of 6 to 12 carbon atoms and the group

a 1,2,4-triazole, benzimidazole, tetrazole, urazole, pyrazole, phthalimido or succinimido group optionally substituted by alkyl of 1 to 4 carbon atoms, alkylmercapto of 1 to 8 carbon atoms, nitro, phenyl and/or benzyl.

* * * * *

UNITED STATES PATENT AND TRADEMARK OFFICE
CERTIFICATE OF CORRECTION

PATENT NO. : 4,362,878
DATED : December 7, 1982
INVENTOR(S) : Terence C. Webb

It is certified that error appears in the above—identified patent and that said Letters Patent is hereby corrected as shown below:

Col. 8, line 37     Delete "(4.44 g," and insert --(4.4g,--

Col. 9, line 6      After "H,7.80" delete ";" and insert -- : --

Col. 11, line 17    Delete "wer" and insert --were--

Signed and Sealed this

Tenth Day of May 1983

|SEAL|

Attest:

GERALD J. MOSSINGHOFF

Attesting Officer    Commissioner of Patents and Trademarks